US009393219B2

(12) United States Patent
Westerhof et al.

(10) Patent No.: US 9,393,219 B2
(45) Date of Patent: Jul. 19, 2016

(54) MONOPHENOLS AND BENZENEDIOLS SENSITIZATION OF IMMUNE SYSTEM AGAINST HAPTENIZED MELANOMA ANTIGENS

(75) Inventors: Wiete Westerhof, Landsmeer (NL); Cornelis Joseph Maria Melief, Haarlem (NL); Rosalie Margaretha Luiten, Abcoude (NL)

(73) Assignees: ACADEMISCH ZIEKENHUIS BIJ DE UNIVERSITEIT VAN AMSTERDAM, Amsterdam (NL); ACADEMISCH ZIEKENHUIS LEIDEN H.O.D.N. LUMC, Leiden (NL)

( * ) Notice: Subject to any disclaimer, the term of this patent is extended or adjusted under 35 U.S.C. 154(b) by 0 days.

(21) Appl. No.: 13/493,284

(22) Filed: Jun. 11, 2012

(65) Prior Publication Data
US 2012/0315304 A1 Dec. 13, 2012

Related U.S. Application Data

(62) Division of application No. 11/996,753, filed as application No. PCT/NL2005/000551 on Jul. 28, 2005, now abandoned.

(51) Int. Cl.
*A61K 31/135* (2006.01)
*A61K 31/05* (2006.01)
*A61K 31/065* (2006.01)

(52) U.S. Cl.
CPC .............. *A61K 31/135* (2013.01); *A61K 31/05* (2013.01); *A61K 31/065* (2013.01)

(58) Field of Classification Search
None
See application file for complete search history.

(56) References Cited

U.S. PATENT DOCUMENTS

| 4,895,727 | A | 1/1990 | Allen |
| 5,395,611 | A | 3/1995 | Jimbow |
| 5,702,694 | A | 12/1997 | Chamness |
| 5,925,332 | A | 7/1999 | Jimbow |
| 6,299,900 | B1 * | 10/2001 | Reed et al. ................... 424/449 |

(Continued)

FOREIGN PATENT DOCUMENTS

| WO | WO 91/16302 | 10/1991 |
| WO | WO 97/01333 | 1/1997 |
| WO | WO 00/25763 | 5/2000 |

OTHER PUBLICATIONS

Radny et al. Phase II trial of intralesional therapy with interleukin-2 in soft tissue melanoma metastases. British Journal of Cancer. 2003, 89, 1620-1626.*

(Continued)

*Primary Examiner* — Anna Pagonakis
(74) *Attorney, Agent, or Firm* — McBee Moore Woodward & Vanik IP, LLC

(57) ABSTRACT

The metabolization of certain phenols, monophenols or benzenediols into reactive quinone compounds, in particular ortho-quinones and related reactive intermediates, which is brought about by oxidation of monophenols and benzenediols by proteins exhibiting tyrosinase activity, such as human tyrosinase and the related proteins TRP1 and TRP2. The compounds function as haptens that become covalently bound to the tyrosinase enzymes, in particular to histidine moieties, in or near the catalytic site of proteins exhibiting tyrosinase activity, such as tyrosinase, TRP1 and TRP2. An immune response is then to be mounted against these haptenized auto-antigens to treat malignancies.

4 Claims, 2 Drawing Sheets

(56) References Cited

U.S. PATENT DOCUMENTS

Figure 1:
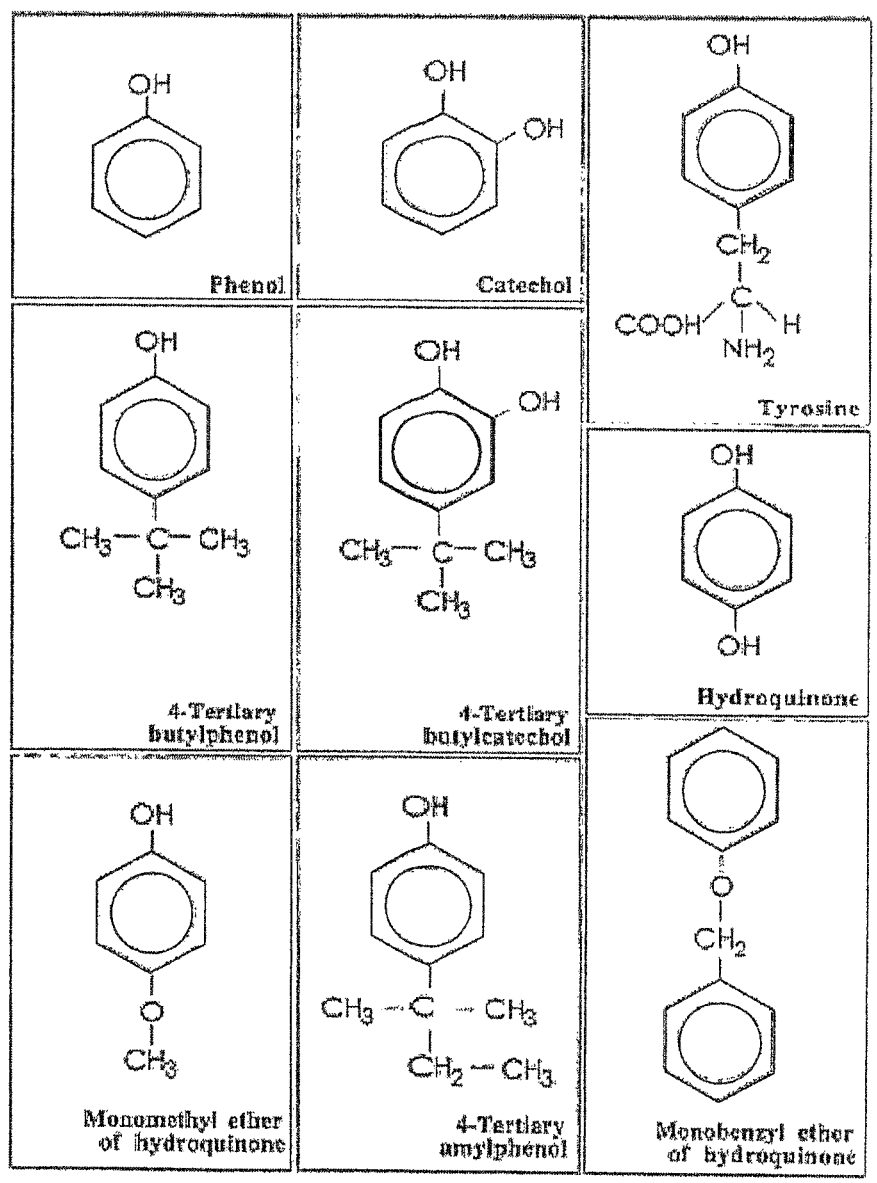

| | | |
|---|---|---|
| 6,528,051 B2 | 3/2003 | Tamarkin et al. |
| 6,562,363 B1 | 5/2003 | Mantelle et al. |
| 2002/0137961 A1 | 9/2002 | Bradley et al. |

OTHER PUBLICATIONS

Vlock et al. Prognostic role of antibody reactivity to melanoma. (J. Clin. Invest. vol. 77, Apr. 1986, 1116-1121).*

Wolf et al. Treatment of lentigo maligna (melanoma in situ) with the immune response modifier imiquimod. (Arch. Dermatol. 2005; 141: 510-514).*

Chavin et al. Survival of mice receiving melanoma transplants is promoted by hydroquinone. Science, vol. 208, Apr. 25, 1980.*

Bowen et al. Apoptosis regulators and responses in human melanocytic and keratinocytic cells. Nature. vol. 120, No. 1 Jan. 2003.*

Radny et al. Phase II trial of intralesional therapy with interleukin-2 in soft tissue melanoma metastases. British Journal of Cancer, 2003, 89, 1620-1626.*

Krieg. From A to Z on CpG. Trends in Immunology. vol. 23, No. 2, Feb. 2002.*

Riley, "Melanogenesis: a Realistic Target for Antimelanoma Therapy?", 1991, pp. 1172-1177.

Thorneby-Andersson, et al., "Tyrosinase-Mediated Formation of a Reactive Quinone from the Depigmenting Agents, 4-tert-Butylphenol and 4-tert-Butylcatechol", 2000, pp. 33-38.

Yang, et al., "The Cytoitoxicity and Apoptosis Induced by 4-Tertiary Butylphenol in Human Melanocytes are Independent of Tyrosinase Activity", 2000, pp. 157-164.

Yee, et al., "Isolation of Tyrosinase-Specific CD8$^+$ and CD4$^+$ T Cell Clones from the Peripheral Blood Melanoma Patients Following in Vitro Stimulation with Recombinant Vaccinia Virus", 1996, pp. 4079-4086.

Fisher et al., Archives of Dermatology, pp. 945-947, 2003.

Richards et al., Combination of chemotherapy with interleukin-2 and interferon alfa for the treatment of metastatic melanoma, Journal of Clinical Oncology, vol. 17, No. 2 Feb. 1999: pp. 651-657.

Mazzocco et al., Analytical Biochemistry, vol. 72, Issues 1-2, May 1976, pp. 643-647, abstract.

Burke et al., Laccases and other polyphenol oxidases in ecto- and ericoid mycorrhizal fungi, Mycorrhiza, 2002,12: 105-116.

Ahmed et al., Imiquimod: a novel treatment for lentigo maligna. British Journal of Dermatology, 2000, 143: 843-845.

Castelli, et al., "Novel HLA-Cw8-Restricted T Cell Epitopes Derived from Tyrosinase-Related Protein-2 and gp100 Melanoma Antigens", 1999, pp. 1739-1748.

Reynolds, et al., "HLA-Independent Heterogeneity of CD8$^+$ T Cell Responses to MAGE-3, Melan-A/MART-1, gp100, Tyrosinase, MC1R, and TRP-2 in Vaccine-Treated Melanoma Patients", 1998, pp. 6970-6976.

Braybrooke et al., "Phase I Study of MetXia-P450 Gene Therapy and Oral Cyclophosphamide for Patients with Advanced Breast Cancer or Melanoma", Feb. 15, 2005, pp. 1512-1520.

Van Den Boorn et al., "Effective Melanoma Immunotherapy in Mice by the Skin-Depigmenting Agent Monobenzone and the Adjuvants Imiquimod and CpG", Plos One, 2010, vol. 5, No. 5, pp. 1-12.

Kirkwood et al., C-581 "Favorable Prognosis of Melanoma Associated with Hypopigmentation (HYP) in a Randomized Adjuvant Trial Comparing DTIC-BCG (D8) VS Monobenzyl Ether of Hidroquinone (HQ) VS Null (NL) treatment", Proceedings of ASCO, vol. 4, p. 149.

* cited by examiner

MONOPHENOLS AND BENZENEDIOLS SENSITIZATION OF IMMUNE SYSTEM AGAINST HAPTENIZED MELANOMA ANTIGENS

CROSS REFERENCE TO RELATED APPLICATIONS

This application is a division of copending application Ser. No. 11/996,753 filed on Jan. 25, 2008; which is the 35 U.S.C. 371 national stage of International application PCT/NL05/00551 filed on Jul. 28, 2005. The entire contents of each of the above-identified applications are hereby incorporated by reference.

FIELD OF THE INVENTION

The invention relates to the field of medicine, in particular to the fields of immunology, autoimmunity and autoantigens. The invention further relates to chemical modification of antigens and methods and means for treatment of neoplastic disease, in particular melanoma.

BACKGROUND OF THE INVENTION

Over the past several decades, the incidence of melanoma has increased at a faster rate than that of any other solid tumor (1). The highest have been observed in Australia and New Zealand (27.9/100,000 among males and 25.0 among females) and in North America (10.9/100,000 among males and 7.7 among females). In 2001, it was estimated that 51 400 cases of invasive melanoma would be diagnosed (2) Early recognition and surgical excision of the primary tumor provide the best opportunity for obtaining a cure. However, prognosis associated with more advanced melanoma remains poor. Patients presenting with thick primary lesions, American Joint Committee on Cancer (AJCC) melanoma stage IIB/C, and those with regional nodal metastases (AJCC melanoma stage III) have a reported 5-year survival ranging from 30 to 70%. This is related to the high failure rates associated with surgical therapy alone in locally and regionally advanced cases. The risk of recurrence after surgery has been reported to be as high as 60% for patients with melanoma stage IIB/C and 75% for patients with melanoma stage III (3). Compounding this, it has been the lack of effective adjuvant therapy, particularly the limited efficacy of cytotoxic chemotherapeutic agents, against melanoma. Recently, the use of high-dose interferon in the adjuvant setting has been reported to improve both disease-free and overall survival (4,5). The benefits of interferon, however, are still being debated, and treatment with interferon is not without significant cost, risk and toxicity. The results achieved with interferon highlight the potential for the immune system to prevent recurrence after surgical resection of high-risk melanomas.

Melanoma has emerged as the primary model for developing immunotherapies for several reasons. Histopathologic evidence of tumor regression is frequently observed within primary melanoma specimens, along with the presence of tumor infiltrating lymphocytes, thus suggesting a prominent role for the immune system in melanoma (6). Melanoma cells readily adapt to tissue culture, resulting in the creation of panels of melanoma cell lines to study. The paucity of effective therapies (chemotherapy, radiation) has resulted in a lower threshold for testing immunological therapies in patients with melanoma (7,8).

For all these reasons, there has been a significant effort to treat malignant melanoma using immunologic modalities. The use of immunotherapy can be categorized as either active or passive. Passive immunotherapy is the use of either antibodies or cells that have previously been sensitized to host tumor antigens. The host need not mount an immune response, the agent will directly or indirectly mediate tumor killing. Active immunotherapy on the other hand is the use of agents that will cause the host to mount an immune response. This can further be broken down to nonspecific and specific active immunotherapies. Nonspecific agents are those that stimulate the immune system globally, but do not recruit specific effector cells. Specific active immunotherapy is designed to elicit an immune response to one or more tumor antigens.

Current strategies for the immunotherapy of melanoma include the induction or enhancement of immune responses against tumor antigens presented by melanosomal proteins such as tyrosinase, tyrosinase related proteins TRP1 and TRP2, gp100, and MART-1. Potent immune responses in humans and animals against melanocytes and these antigens, comprising melanocyte eradicating CTL responses as well as humoral responses, have been observed in autoimmune depigmenting disorders.

Vitiligo is one such acquired depigmenting disorder, and is characterized by the loss of melanocytes from the epidermis. Several types of vitiligo are distinguished according to the distribution of the achromic lesions. One or more lesions in a quasidermatomal pattern are characteristic for unilateral vitiligo while this unilateral distribution is absent in focal vitiligo. Both are localized types of vitiligo. Generalized vitiligo is characterized by multiple scattered lesions in a symmetrical distribution pattern. The course of the disease is unpredictable but is often progressive with phases of stabilized depigmentation (9). An extending vitiligo with enlarging lesions or development of new lesions is defined as active vitiligo.

The association with autoimmune disorders and organ specific antibodies as well as the fact that non-surgical repigmenting therapies have immune-modulating effects also support the idea of an autoimmune pathogenesis of the disease. The humoral antibodies are generally considered to be an epiphenomenon. Progress in the understanding of the pathogenesis of vitiligo emerges from studies on the local phenomena leading to or related with the process of depigmentation. The normal appearing skin adjacent to the depigmented area is histologically characterized by degenerative changes in melanocytes, vacuolar changes of basal cells, the presence of a lymphocytic infiltration in epidermis and dermis as well as melanophages in the upper dermis (10-12). In progressing inflammatory vitiligo, which is characterized by achromic lesions surrounded by a red raised rim, the lymphocytic infiltration proceeds in the direction of skin that still contains melanocytes, suggesting a role of the inflammatory infiltrate in melanocyte disappearance (13). A recent study localized CLA+ cytotoxic T cells in apposition to disappearing melanocytes in the perilesional skin of generalized vitiligo. Also, a focal, epidermal expression of ICAM-1 and HLA-DR at the interaction site between skin homing T cells and melanocytes was detected (14). HLA-DR expression implicates the involvement of MHC class II-restricted T cells in the pathogenic process (15). Perilesional T-cell clones (TCC) derived from patients with vitiligo exhibited a predominant Type-1-like cytokine secretion profile, whereas the degree of Type-1 polarization in uninvolved skin-derived TCC correlated with the process of microscopically observed melanocyte destruction in situ. Detailed analysis of broad spectrum of cytokines produced by perilesional- and nonlesional-derived CD4+ and CD8+ TCC confirmed polarization toward Type-1-like in both CD4 and CD8 compartments, which paralleled depigmentation process observed locally in the skin. Furthermore, CD8+ TCC derived from two patients also were analyzed for reactivity against autologous melanocytes. The antimelanocyte cytotoxic reactivity was observed among CD8+ TCC isolated from perilesional biopsies of two patients with vitiligo. Finally, in two of five patients, tetramer analysis revealed presence of high frequencies of Mart-1-specific CD8 T cells in T-cell lines derived from perilesional skin (16).

One distinctive form of vitiligo is contact or occupational vitiligo (17,18). This form is unique in that its onset correlates with exposure to certain chemicals that induce chemical leukoderma. Contact/occupational vitiligo is distinct from chemical leukoderma in that the initial cutaneous depigmentation extends from the site of chemical contact and subsequently develops into progressive, generalized vitiligo (19). There is anecdotal and experimental evidence demonstrating that certain environmental chemicals are selectively toxic to melanocytes, both in culture and in vivo (20,21,22) and are thus responsible for instigating vitiligo (19). The majority of these toxins are aromatic or aliphatic derivatives of monophenols and benzenediols, containing a phenylring substituted with 1 or 2 hydroxyl moieties, which may be in the ortho-(1 and 2, catechols), meta-(1 and 3; 1,3 benzenediol is also referred to as resorcinols) and para-(1 and 4) configurations, such as para-hydroxybenzene, also referred to as hydroquinone (FIG. 1). Table 1 lists a selection of preferred monophenols, benzenediols and/or catechols (or 1,2 dihydroxyphenyl compounds) and sulfhydryls capable of depigmenting skin and/or instigating vitiligo. Some of these compounds have been added to bleaching creams, products used to remove hyperpigmented lesions. Interestingly, these creams are not toxic to melanocytes from all individuals. Even at high dosages only a subset of humans depigment in response to application. Exposure of the skin to certain phenols and catechols such as Monobenzyl ether of hydroquinone (MBEH), 4-tert-butylphenol (TBP) and 4-tert-butylcatechol (TBC) causes leukoderma and can induce vitiligo-like depigmentation. Many of the cases have been reported by workers who were exposed to these compounds in the polymer or leather industries. MBEH, TBP, TBC and other monophenols or benzenediols are substrate analogs that can be oxidized by enzymes having tyrosinase activity, yielding quinones and in particular orthoquinone intermediates, compounds that are highly reactive and which rapidly react with cystein and/or histidine moieties in proteins. In particular, some high reactive orthoquinones will immediately react with cysteine or preferably histidine residues moieties in the vicinity of or more preferably within the catalytic site of the tyrosinase enzyme.

Thus far the results of treatment for metastatic melanoma have been disappointing. Single-agent chemotherapy produces response rates ranging from 8% to 15%, and combination chemotherapy, from 10% to 30%. These responses are usually not durable. Immunotherapy, using interferon (IFNγ) or particularly high-dose interleukin (IL)-2, has also shown a low response rate of approximately 15%, although it is often longer-lasting. In fact, a small but finite cure rate of about 5% has been reported with high-dose IL-2. Phase II studies of the combination of cisplatin-based chemotherapy with IL-2 and interferon-alfa, referred to as biochemotherapy, have shown overall response rates ranging from 40% to 60%, with durable complete remissions in approximately 8% to 10% of patients. Although the results of the phase II single-institution studies were encouraging, phase III multicenter studies have reported conflicting results, which overall have been predominantly negative. Moreover, IL-2 and IFN administration are associated with multiple side effects, and only physicians experienced in the management of such therapies should administer them.

Riley (23,24) applied the depigmenting phenol compound 4-HA (4-hydroxyanisole) as a chemotherapeutic in melanoma, without success. Attempts to use these agents for the treatment of disseminated melanoma have foundered on problems due to unfavorable pharmacokinetics, primary toxicity or pharmacological actions of analogue substrates, and toxicity of hepatic metabolites. The intra arterial infusions in the lower limbs gave rise to serious renal and hepatic toxicity.

Novel strategies are clearly needed to improve the clinical outcome of melanoma. The use of the autoantigens responsible for the autoimmune disorder vitiligo for the induction of an anti-tumor response has since long been investigated. So far, this has not yielded improved therapies and medicaments for the treatment of melanoma. Similarly, the studies of Riley and others concerning the use of compounds capable of inducing occupational vitiligo and cytotoxicity against melanocytes for the treatment of melanoma have not been successful. The current inventors aimed to overcome the current status quo. The current invention is based on new insights in how antigens present in melanocytes may be chemically modified and activated in situ, providing new methods and means for the treatment of tyrosinase expressing malignancies such as melanoma.

SUMMARY OF THE INVENTION

Administration of certain phenols, comprising monophenols, in particular para-hydroxylated, meta-hydroxylated, ortho-hydroxylated monophenols and benzenediols, more in particular catechols (ortho: 1,2), recorcinols (meta: 1,3) and hydroquinones (para: 1,4), also possibly substituted with side chains. These phenol compounds of the invention by definition must be able to function as substrate analogs for tyrosinase, for the treatment of melanocyte related diseases such as hyper-pigmentary disorders, and have been assayed by several scientists and clinicians (see table 1). Adrenalin, noradrenalin and semiquinones of estrogens are also known to be substrate for tyrosinase enzymes.

Although 4-Hydroxyanisole was used in the treatment of metastatic melanoma, the intra arterial infusion of high doses of 4-Hydroxyanisole was proven not effective and lead to severe toxic events. The intra arterial infusion of monophenols and benzediols bypasses the melanocyte in the skin or the melanoma cell in the skin or in the malignant lesion. The current invention is based in part on the observation that monophenols or benzenediols need to be metabolized into reactive quinones, in particular ortho-quinones and related reactive intermediates, which is brought about by oxidation of monophenols and benzenediols by proteins exhibiting tyrosinase activity, such as human tyrosinase and the related proteins TRP1 and TRP2. Although the substances and the produced reactive intermediates are toxic and can induce cell death directly, it is more relevant according to this invention that they function as haptens that become covalently bound to the tyrosinase enzymes, in particular to histidine moieties, and to a lesser extent cystein moieties, in or near the catalytic site of proteins exhibiting tyrosinase activity, i.e. tyrosinase, TRP1 and TRP2.

Contrary to the high doses of tyrosinase surrogate substrates used in case of intra arterial infusions as a chemotherapy, a thousand fold lower systemic concentration is achieved in the current invention by local application of the active compounds on the lesions or injection in the melanoma lesion, to evoke sensitization of the immune system against melanoma cells. The intra arterial infusion of monophenols and benzenediols, in particular catechols, bypasses the melanoma cell in the skin or in the malignant lesion. The invention comprises the use of 'haptenized' proteins, in particular proteins exhibiting a tyrosinase activity and fragments of those proteins, which may be applied for eliciting immune responses in vivo or in vitro and for the manufacture of medicaments or vaccines. In particular embodiments of the invention, the reaction of the immune system of a subject to be treated for pigment cell malignancies such as melanoma, is further stimulated by immune modulators applied on or in the lesion, for instance compounds eliciting a local inflammatory response. In a most preferred embodiment, the method and medicaments of the invention are applied in conjunction with steps to decrease the presence or the activity of regulatory T cells. Regulatory T cells function to prevent autoimmunity and hamper attempts to elicit an immunogenic response against auto-antigens derived from melanocytes such as tyrosinase and tyrosinase related proteins TRP1 and TRP2. The invention provides different optional measures and steps to minimize the obstruction of regulatory T cells in the process of generating a cellular immunogenic response against the modified autoantigens of the invention.

DETAILED DESCRIPTION

The syndrome of occupational vitiligo provides information about autoantigens that may aid in mounting an effective immune response against any cell comprising tyrosinase activity and/or a melanin metabolism, in particular malignant melanoma cells, involving T cell and optionally B cell responses.

The hypothesis, that monophenols and benzenediols are substrates of tyrosinase and that they are converted to reactive quinones as the reactive species responsible for melanocyte toxicity, is generally accepted (17), although disputed by others (25). Monophenols and benzenediols are structurally similar to tyrosine, the substrate for tyrosinase that initiates the biochemical pathway for melanin synthesis (FIG. 2) (22). Derivatives of monophenols and benzenediols (so-called surrogate substrates) compete with tyrosine for hydroxylation by tyrosinase and interfere with melanin synthesis (26,27,28,29) and corresponding semiquinone free radicals are generated by the catalytic action of tyrosinase on these phenolic/catecholic derivatives.

Tyrosinase (E.C.I.14.18.1) exhibits unusual kinetics, the oxidation of its primary substrate, the monohydric phenol tyrosine, is characterized by a lag period (30), which is extended with increasing substrate concentration. The attainment of the maximum velocity of reaction is dependent on the recruitment of enzyme in the met state. In the met enzyme the two copper atoms at the active site are in the Cu(II) form and are unable to form a complex with molecular oxygen (31). The process of "recruitment" involves reduction of the active site copper atoms to the Cu(I) form, which permits the binding of oxygen in a peroxy conformation (32). This oxy enzyme is able to catalyze the oxidation of monohydric phenol substrates such as tyrosine. Although alternative reductants are known (33,34,35), reduction of active site copper atoms is most efficiently brought about by dihydric phenol (such as catecholic) substrates such as 3,4-dihydroxyphenylalanine, which are oxidized to the corresponding ortho-quinone in the process (dopaquinone). The autoactivation of tyrosinase is thus explained by the generation of activating catechol in the process of monohydric phenol oxidation and the prolongation of the lag period with increasing substrate concentration results from competition for the active site between the monohydric phenol and the enzyme-recruiting catechol (36). The highly related TRP1 and TRP2 proteins exhibit different substrate specificities and kinetics from tyrosinase. They have also been reported to use different cofactors such as $Zn^{2+}$ or $Fe^{2+}$. Whereas tyrosinase catalyzes the rate-limiting generation of L-dopaquinone from L-tyrosine and is also able to oxidize L-DOPA to L-dopaquinone, the mouse TRP1, but not tyrosinase, catalyzes the oxidation of the indolic intermediate 5,6-dihydroxyindole-2-carboxylic acid (DHICA) into the corresponding 5,6-indolequinone-2-carboxylic acid, thus promoting the incorporation of DHICA units into eumelanin. The catalytic activities of the human melanogenic enzymes are still debated. It is clear however that also TRP1 and TRP2 show reactivity towards most or all of the monophenols and benzenediols, in particular catechols, that are also tyrosine substrate analogs that can be metabolized by tyrosinase.

The current inventors observed the histology of skin of vitiligo patients undergoing depigmentation therapy with Monobenzone (monobenzyl ether of hydroquinone or p-(benzyloxy)phenol) and noticed a dense infiltrate consisting of mainly $CD8^+$ cells and macrophages indicating a delayed type cell mediated immune response and no granulocytes, which would have been there in case of a toxic (orthoergic) reaction. In vitro melanocytes and keratinocytes are equally sensitive to the toxic effects of Monobenzone but in vivo it is observed that an inflammatory response with erythema, edema and scaliness is only seen in the pigmented skin. No reaction occurs in depigmented skin. This entails that the inflammatory reaction is directed towards something, what is only present in melanocytes, e.g. tyrosinase, TRP1 and/or TRP2. However, auto-antibodies to tyrosinase, TRP1 and TRP2 have been reported to occur at low frequencies, or not at all, in vitiligo patients (37,38,39,40,41).

To stage an effective immune response against autoantigens it may be necessary to modify an autoantigen as the immune systems selects against recognition of self antigens. Both B and T cells undergo positive and negative selection in the primary lymphoid organs, in particular in the thymus. Positive selection requires signaling through the antigen receptor for the cell to survive. Developing B cells are positively selected when the pre-B receptor binds its ligand. Developing T cells are positively selected for their ability to bind MHC as well as peptide. Negative selection means that binding to the receptor results in cell death. Both immature B and T cells are negatively selected if they bind self antigen. Therefore, in order to stage an effective immune response against autoantigens one approach would be to slightly change or modify an autoantigen. This apparently happens in the body in case of various autoimmune diseases, often triggered by an infection or by exposure to chemicals. So far the exact nature of such altered auto-antigens are not known. However much is known already about the interaction of (ortho-)quinones and tyrosinase, which can be brought about by exposure to various monophenols and benzenediols, prime examples are listed in table 1.

TABLE 1

Selected chemicals associated with contact/occupational vitiligo
Adapted from Miyamoto and Taylor (22).

| Most potent phenol/catechol derivatives | Additional phenol/catechol derivatives |
|---|---|
| Monobenzyl ether of hydroquinone | Monomethyl ether of hydroquinone (p-methoxyphenol; p-hydroxyanisole) |
| Hydroquinone | Monoethyl ether of hydroquinone |

TABLE 1-continued

Selected chemicals associated with contact/occupational vitiligo
Adapted from Miyamoto and Taylor (22).

| Most potent phenol/catechol derivatives | Additional phenol/catechol derivatives |
| --- | --- |
| (1,4-dihydroxybenzene; 1,4-benzenediol; quinol; p-hydroxyphenol) | (p-ethoxyphenol) |
| p-tert-Butylchatechol | p-Phenylphenol |
| p-tert-Butylphenol | p-Octylphenol |
| p-tert-Amylphenol | p-Nonylphenol |
| | p-Isopropylcatechol |
| | p-Methylcatechol |
| | Butylated hydroxytoluene |
| | Butylated hydroxyanisole |
| | Pyrocatechol (1,2-benxenediol) |
| | p-Cresol |
| | Sulfhydryls |
| | β-Mercaptoethylamine hydrochloride (cysteamine) |
| | N-(2-mercaptoethyl)-dimethylamine hydrochloride |
| | Sulfanolic acid |
| | Cystamine dihydrochloride |
| | 3-Mercaptopropylamine hydrochloride |

Occupational vitiligo caused by for instance monobenzone (MBEH) or by any one of the monophenols and benzenediols listed in table 1, exemplifies how autoantigens involved in melanine metabolism are to be changed. MBEH and other related compounds are substrates of tyrosinases, capable of reacting at the catalytic site of the enzyme, and culminating in a 'suicide' reaction with the enzymes catalytic site. After a catalytic reaction the monobenzone is oxidized into an ortho-quinone (benzyl oxy orthoquinone). This extremely reactive compound binds covalently with histidine residues at the mammalian enzyme's active site (42). The compound or its remains are trapped in the catalytic domain of the enzyme and this leads to suicide inactivation of the enzyme. When a monophenol such as MBEH or 4-PTB or a benzenediol or any other related compound to the examples listed in table 1, is covalently bound to tyrosinase, this will give rise to modified antigens.

The current invention is based on the observation that the complex of the enzyme and phenol; monophenol or benzenephenol, can subsequently be metabolized inside a proteasome of a cell comprising tyrosinase activity and treated with the monophenol or benzenediol, such as a melanocyte, and will be displayed by MHC class 1 molecules on its surface. The Langerhans cells, dendritic cells in the skin, pick up antigens and process it into an 8-mere or 9-mere (or a polypeptide of even 10 to 12 or more aminoacids). In the regional lymph node this specific polypeptide will subsequently be presented to memory cells within the restrictions of the Major Histocompatibility Complex. Cytotoxic $CD8^+$ cells are then generated, which have homing properties, staging the immune response in the original area defined by receptors on endothelial cells of small blood vessels causing the extravasations of these cytotoxic T-cells. Vitiligo-like depigmentation will then ensue in the region by the attack of the cellular immune system against cells displaying the modified autoantigens.

In case of the desired sensitization of the immune system of a melanoma patient with a composition according to the invention, comprising monophenol or benzenediol compounds, the T-cell mediated cytotoxicity will be directed toward cells displaying the modified autoantigens, such as melanocytes, especially when the compound is applied topically on the lesion or injected intralesionally at relatively low doses. It will be particularly advantageous to repeat the administration to provide a continuous exposure of modified antigen to the immune system and thereby boost the immune response. More preferably, a slow release formulation of the phenol or catechol may be applied, providing a prolonged and sustained exposure, while at the same time avoiding the toxicity of high peak doses of the compound to be used. During and after treatment, all cells having a melanin metabolism, including normal melanocytes in the skin and hair, will disappear, locally and/or even systemically. This depigmenting effect is an unwanted but in the case of malignant and metastasizing melanoma an acceptable side effect of the treatment.

Hence, in a first embodiment, the current invention provides medicaments for the treatment of melanoma and diseases, in particular neoplastic diseases, caused by melanocytes and melanocytic nevus cells exhibiting tyrosinase enzyme activity. The invention teaches the use of phenols, in particular certain monophenols and benzenediols compounds that can function as substrate analogues of tyrosine and that are capable of reacting with enzymes exhibiting tyrosinase activity via reactive intermediates, especially ortho-quinones and will inactivate tyrosinase or related proteins and modify it through covalent binding. The monophenols and benzenediols can be used for the manufacture of medicaments for the treatment of malignancies exhibiting tyrosinase enzyme activity, such as but not limited to melanoma cells and melanocytic nevus cells, whereby the medicament is suitable for direct topical administration on the lesions comprising the cells with tyrosinase activity. Topical administration is an essential feature of the invention, in order to bring the proteins involved in melanin metabolism, such as tyrosinase, TRP1 and TRP2, in direct contact with the substance(s). Topical administration may take place directly on the skin, on healthy or normal skin or preferably on, in or around lesions on or in the skin, i.e. on the melanomas or nevi to be treated. Systemic administration would require higher and potentially toxic doses of the active compounds and would result in severe side effects caused by premature reaction and interaction of the drug in body parts, organs and tissues where this is not desirable or helpful. Moreover, systemic administration may lead to premature metabolisation of the compounds and/or the compounds will be cleared from circulation, as it will be removed by the liver and the kidney (first pass effect), and thereby never reach it's target cells having tyrosinase activity and residing predominantly in, on or under the skin. More distant metastases of melanomas will be reached by the CTL response, throughout the body. The method and compositions according to the invention are primarily aimed at the treatment of melanoma, but may also be applied to treat pre-melanoma lesions, congenital melanocytic nevi (e.g. Giant Hairy nevus), melanocytic nevi e.g atypical or dysplastic nevi, cellular blue nevus and Becker's nevus, all of which are known to be capable of becoming malignant.

The phenol compound to be used may be selected from the groups of mono-phenols, benzenediols and especially catechols that are known in the art to be capable of inducing vitiligo and are known to be substrates of tyrosinase, TRP1 and/or TRP2. Many of these compounds have been described in the art. Monophenols and benzenediols or dihydroxybenzenes are aromatic chemical compounds in which one or two hydroxyl groups are substituted onto a benzene ring. Because they have at least one hydroxyl group covalently bonded directly to a carbon atom in a benzene ring, they are in a class of organic compounds called phenols. There are three isomers of benzenediols, each of which a has its own common or non-systematic name as shown in the table 2 below. Various other ways of naming these three chemical compounds are also shown:

TABLE 2

| benzenediols: | | |
|---|---|---|
| ortho isomer | meta isomer | para isomer |
| 1,2-benzenediol | 1,3-benzenediol | 1,4-benzenediol |
| o-benzenediol | m-benzenediol | p-benzenediol |
| 1,2-dihydroxybenzene | 1,3-dihydroxybenzene | 1,4-dihydroxybenzene |
| o-dihydroxybenzene | p-dihydroxybenzene | p-dihydroxybenzene |
| chatechol (or catechol) | resorcinol | hydroquinone |
| pyrochatechol | | |

All three of these compounds are colorless to white granular solids at room temperature and pressure, but upon exposure to oxygen they may darken. All three isomers have the chemical formula $C_6H_6O_2$. Similar to other phenols, the hydroxyl groups on the aromatic ring of a benzenediol are weakly acidic, depending on other substituents on the phenyl ring. Each benzenediol can lose an $H^+$ from one of the hydroxyls to form a monophenolate ion or lose an $H^+$ from both to form a diphenolate ion.

Hydroquinone can undergo mild oxidation to convert to the compound parabenzoquinone, $C_6H_4O_2$, often called p-quinone or simply quinone. Reduction of quinone reverses this reaction back to hydroquinone. Some biochemical compounds in nature have this sort of hydroquinone or quinone section in their structures, such as Coenzyme Q, and can undergo similar redox interconversions. Hydroquinone has a variety of uses principally associated with its action as a reducing agent which is soluble in water. It is a major component in most photographic developers where, with the compound Metol, it reduces silver halides to elemental silver.

The monophenols and dihydroxybenezenes that can function as substrate analogues for tyrosinase may have one or more substituents of the phenyl ring, which will alter the reactivity and specificity of the compound for its tyrosinase target enzyme. Substituents may comprise methoxy, ethoxy, methyl, ethyl, propyl, butyl, amino, carbonyl, phenyl, sulfhydryl, halogens and many other chemical groups or substituents. The various compounds may differ in their (bio)chemical reactivity, stability, toxicity and most importantly their immunogenicity as a hapten on tyrosinase. A selection of suitable examples of vitiligo inducing compounds is listed in table 1 in this specification. According to this invention, the following list of phenol compounds are preferred for haptenization of tyrosinase enzymes: from the group of monophenols and benzenediols; phenol, catechol, hydroquinone, 4-tertiary butylphenol, 4-tertiary amylphenol, 4-tertiarybutylcatechol, monomethyl ether of hydroquinone, monoethyl ether of hydroquinone, 4-tertiary amylphenol, monobenzyl ether of hydroquinone, 4-phenylphenol, 4-octylphenol, 4-nonylphenol, 4-isopropylcatechol, 4-methylcatechol, p-cresol, 1,2-benzenediol, butylated hydroxyanisole, butylated hydroxytoluene, 4-S-cysteaminylphenol, N-acetyl-4-S-cysteaminylphenol. Most preferred compounds are monobenzone (MBEH) and 4-PTB (4-paratertiary butylphenol) which have a very high potency of inducing vitiligo. Also sulfhydryls such as mercaptoethylamine hydrochloride (cysteamine), N-(2-mercaptoethyl)-dimethylamine hydrochloride, cystamine dihydrochloride, 3-mercaptopropylamine hydrochloride and sulfonic acid are most suitable for use according to this invention.

In other embodiments two or more compounds of the group of monophenols and benzenediols may be used in combination, simultaneously in one composition or in separate compositions, simultaneously or sequentially applied to the lesion in situ. The use of several compounds has the advantage that the auto-antigen providing proteins that have tyrosinase activity, will be modified with several compounds and/or reactive intermediates. Thereby several different 'haptens' on the tyrosinase enzymes will provide immune systems of treated subjects with a wider range of potential antigens that can be taken up and displayed by HLA molecules. Since the 'fit' of an antigen is among other factors highly dependent on HLA isotypes, this broadened approach will boost the potential immune response significantly. The mounting of a systemic autoimmune reaction against all cells having tyrosinase activity provides an excellent means to combat also distant metastases, even micrometastases, that are not accessible to surgical methods or radiotherapy and which are not accessible for topical drug administration. The capability of melanomas to spread out and to form local and distant metastases is a common problem in treatment of patients suffering from malignant melanomas. This problem can be effectively eliminated with the methods and medicaments of this invention.

Figure 2:
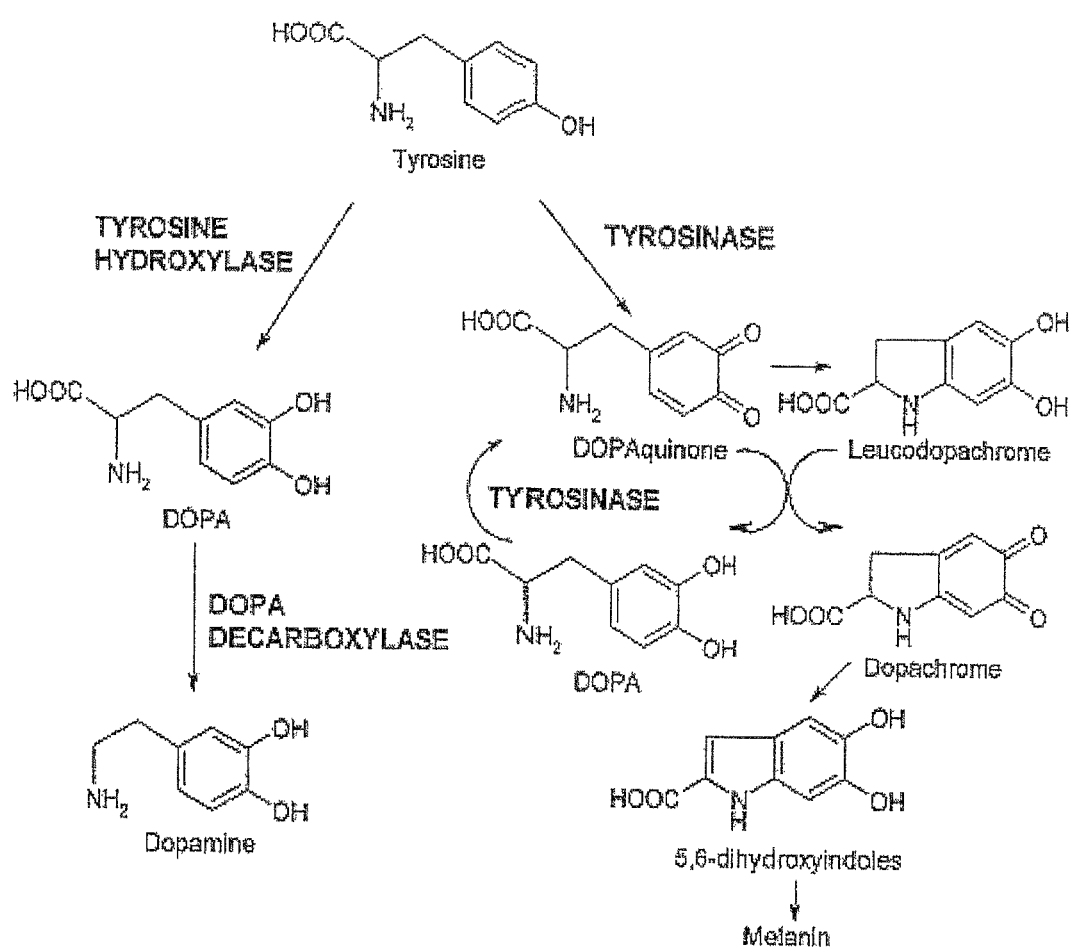

The proteins to be modified with the monophenol or benzenediol (=diphenol) compounds and thereby to be converted into an entity capable of inducing autoimmune responses, are proteins that are highly specific for cells having a melanin metabolism. These cells primarily comprise normal melanocytes, melanocytic nevus cells or malignant melanoma cells. Proteins known to be specific for melanocytes and melanoma cells and proteins which are known to be involved in the autoimmune disorder vitiligo, and can function as auto-antigens, comprise at least tyrosinase (E.C.I.14.18.1), tyrosinase related proteins 1 and 2 (TRP1 and TRP2), but may also comprise other, yet to be identified proteins that are also capable of exhibiting tyrosinase activity or enzymatic activity further down stream in the melanogenesis pathway (FIG. 2).

The invention thus provides melanocyte and/or melanoma cell specific 'haptenized' auto-antigens. The induction of an immune response against these haptenized auto-antigens according to the invention may be enhanced, accelerated, prolonged by the prior, simultaneous or subsequent use of immune modifying compounds. It is an object of the invention to elicit an auto-immunity response against these antigens, which may be enhanced by compounds capable of activating or stimulating immune responses, such as various adjuvants and immune modifiers known in the art. In one embodiment, the use of compounds or compositions that are able to recruit lymphocytes to the treated lesion, activate professional antigen presenting cells (such as dendritic cells or langerhans cells), may be combined with the treatment and the compositions according to the invention. For instance Toll like receptor (TLR) activating compounds and/or adjuvants such as LPS, lipid A, peptidoglycans, flagellins, dsRNA, ssRNA, CpG DNA, Pam3Cys or immunemodifyers such as imiquimod or resiquimod, CD40 ligands or activating antibodies may be systemically, but preferably topically, applied to stimulate a local inflammatory response in the lesion treated according to the invention. Adjuvants may also be advantageously used in combination with the invention. Furthermore, compounds such as cytokines (interleukins), chemokines and interferons that stimulate, enhance or prolong an immune response against the modified or 'haptenized' autoantigens of the invention may be applied. This can be done by providing them directly or by stimulating their local synthesis or release. Particularly the use of interferon gamma and interleukins may be used to stimulate the generation of a cellular and humoral immune response against the antigens of the invention, in particular by recruitment and activation of professional antigen presenting cells.

In a particularly preferred embodiment of the invention, the method of treatment comprising the sensitization against haptenized tyrosinases by chemical modification is combined with steps to reduce or abolish the function of regulatory T cells. Regulatory T cells actively suppress the induction of autoimmune responses. The skilled person can choose from several methods and compounds that are capable of inhibiting regulatory T cells ($CD4^+/CD25^+$ T-cells). In particular the use of fludarabine, cyclophosphamide and related chemotherapeutic compounds are preferred means for reducing the number and the activity of regulatory T cells and the breaking of tolerance for the modified auto-antigens according to this invention. In order to enhance T cell activation during immunization, blocking cytotoxic T lymphocyte-associated antigen 4 (CTLA-4), a critical receptor that down regulates T cell activation, may be applied. Prior treatment with CTLA-4 before with the melanocyte-specific haptenized antigens of the invention is particularly preferred.

A pharmaceutically acceptable composition according to the invention comprises at least one monophenol or benzenediol compound that can function as a substrate analogue of tyrosine and is capable of reacting with proteins exhibiting tyrosinase activity; tyrosinase proteins or tyrosinase related proteins 1 and 2, or which can be activated by these enzymes into a reactive intermediate which can subsequently react with tyrosinase or other related proteins. Optionally the composition may comprise one or more compounds selected from immune modifying compounds, immunogenic adjuvants and pharmaceutical excipients. Pharmaceutical excipients may comprise any excipient known and customary in the art and for instance described in Remington; The Science and Practice of Pharmacy, $21^{nd}$ Edition 2005, University of Sciences in Philadelphia. Pharmaceutical compositions and medicaments of the invention may thus comprise binders such as lactose, cellulose and derivatives thereof, polyvinylpyrrolidone (PVP), humectants, disintegration promoters, lubricants, disintegrants, starch and derivatives thereof, sugar solubilizers, anti-oxidants, preservatives, immuno-stimulatory adjuvants or other excipients. The invention provides methods and means to formulate and manufacture new medicaments and/or pharmaceutical formulations for the treatment of melanomas by topical administration to sensitize the immune system against melanoma antigens. The composition is preferably a composition that is optimized for transepidermal delivery, and may comprise skin penetrants or permeators and skin-permeation enhancers such as organic solvents such as DMSO, ethanol, or propylene glycol, whereby the resulting medium (skin/solvent) may have an increased partition coefficient for the therapeutic compound(s). In another embodiment the composition is a so called slow release formulation, which are known per se in the art of pharmacy, and may for instance comprise a release controlling polymer, -gel or -matrix, forming a depository of the active compound(s) (i.e. the monophenols and/or benzenediols), optionally surrounded or coated with a release controlling coating or membrane or biodegradable polymer, providing a slow but continued administration and/or release of the active compounds. Topical delivery compositions comprise ointments, pastes, gels, medicated powders, creams, lotions, aerosols, sprays, foams and medicated adhesives. Medicated adhesives, such as depositories on patches, allow a sustained delivery of the drug over days in many cases at a constant rate. Alternatively, the composition may also comprise a pharmaceutically acceptable liquid formulation which may be injected directly into the lesion.

In another embodiment, the invention provides modified or 'haptenized' proteins and antigens. The haptenized proteins according to the invention, tyrosinase and tyrosinase related proteins 1 and 2 (TRP1 and TRP2), may be isolated from in vitro sources or in vivo sources, i.e. isolated from eukaryotic expression in cells or from (skin-)tissues, or from expression in transgenic micro-organisms cells. The proteins may be modified in vivo but also in vitro bringing them in contact with the phenol and catechol compounds described before, under conditions conducive to reacting with the tyrosinase or related proteins, to provide a source of haptenized proteins. These haptenized proteins, in particular tyrosinase enzymes and fragments thereof, will be useful for the manufacture of melanoma vaccination compositions and medicaments. Such medicaments are directed at vaccination strategies and are capable of eliciting immune responses against these haptenized autoantigens in a subject. The haptenized proteins or fragments thereof, may be incorporated in vaccine compositions, suitable for administration to subjects suffering from melanoma or at risk of developing melanomas, in which an autoimmune response against melanocytes and/or malignant melanoma cells is to be raised.

In yet another embodiment the current invention provides T cells and T cell receptors, that are specific for the haptenized antigens of the invention. These T cells and T cell receptors may be isolated from subjects treated with the methods and medicaments according to this invention. The isolated T cells may be propagated in vitro, optionally immortalised, via standard laboratory techniques. The genes encoding these T cell receptors may be cloned from these T cells via standard recombinant DNA techniques known in the art (Sambrook, Molecular Cloning, $3^{rd}$ edition, CSH press 2001, Ausubel et al., Short Protocols in Molecular Biology, John Wiley & Sons, 4th edition, 1999). Cloned T cell receptors can be readily transferred to autologous T cells from any subject to be treated for melanomas or other malignancies involving cells with a melanin metabolism. T cell transfer techniques are well documented in the art. T cells specific for melanoma antigens obtained directly from subjects treated according to the invention, or obtained after transfer of the gene encoding the T cell receptor, may be used for compositions to treat subjects suffering from malignancies expressing tyrosinase, such as (primary melanoma's) and/or metastases from melanoma's.

FIGURE LEGENDS

FIG. 1. Monophenols and benzenediols are structurally similar to tyrosine, the substrate for tyrosinase that initiates the biochemical pathway for melanin synthesis.

FIG. 2. Symplified scheme of melanin metabolism.

EXAMPLES

Example 1

Cream Formulation and Applications 10-20% Monobenzone in Lanette cream, which was applied (once) daily; by topical application to the skin overlying and surrounding the melanoma lesion during 14 consecutive days, followed by tumor excision or resection. Reapplication of the cream in order to booster the immunity was performed every 2 weeks.

Injection fluid: 1-5% Monobenzone was dissolved in ethanol and subsequently diluted in water. The composition was injected inside the melanoma tumor or metastases or in a melanocytic nevus and reapplication every 2 weeks during 3 months to booster the response.

Any other monophenol or benzenediol (surrogate substrates) metabolized by tyrosinase into an orthoquinone can replace Monobenzone as the active ingredient. Also a mixture of two ore more surrogate substrates could be utilized for the sensitizing formulation. The concentration of the active constituents may vary from 0.1% to 20%.

The formulated cream and injection fluid (carrier substances) can be replaced by all other known carrier substances and application methods. The cream may for instance comprise a mixture of water, cetyl alcohol, propylene glycol, sodium lauryl sulfate and wax.

The time schedule of the application procedure for inducing sentization against melanoma or melanocytic nevi may be readily adapted by the treating physician according to the clinical response and results, but in general preferably comprises a daily administration of the active compound for at least 1 week, preferably 2 to 8 weeks.

REFERENCES

1. Michael S. Sabel and Vernon K. Sondak. Tumor Vaccines: A Role in Preventing Recurrence in Melanoma? Am J Clin Dermatol 2002; 3:609-616
2. Greenlee R T, Hill-Harmon M B, Murray T, et al. Cancer statistics 2001. CA Cancer J Clin 2001; 51: 15-36
3. Balch C M, Buzaid A C, Soong S J, et al. Final version of the American Joint Committee on Cancer Staging System for Cutaneous Melanoma. J Clin Oncol 2001; 19 (16): 3635-48
4. Kirkwood J M, Strawderman M H, Ernstoff M S, et al. Interferon alfa-2b adjuvant therapy of high-risk resected cutaneous melanoma: the Eastern Cooperative Oncology Group Trial EST 1684. J Clin Oncol 1996; 14: 7-17
5. Kirkwood J M, Ibrahim J G, Sosman J A, et al. High-dose interferon alfa-2b significantly prolongs relapse-free and overall survival compared with the GM2-KLH/QS-21 vaccine in patients with resected stage IIB-III melanoma: results of intergroup trial E1694/S9512/C509801. J Clin Oncol 2001; 19: 2370-80
6. Leong S P L. Immunotherapy of malignant melanoma. Surg Clin North Am 1996; 76 (6): 1355-81
7. Wolchok J D, Livingston P O. Vaccines for melanoma: translating basic immunology into new therapies. Lancet Oncol 2001; II: 205-11
8. Houghton A N, Gold J S, Blachere N E. Immunity against cancer: lessons learned from melanoma. Curr Opin Immunol 2001; 13 (2): 134-40
9. Njoo M D, Westerhof W. Vitiligo: Pathogenesis and treatment. Am J Clin Dermatol 2001; 2:167-181
10. Hann S K, Park Y K, Lee K G, Choi E H, Im S. Epidermal changes in active vitiligo. J Dermatol 1992; 19:217-222
11. Moellmann G, Klein-Angerer S, Scollay D A, Nordlund J J, Lerner A B. Extracellular granular material and degeneration of keratinocytes in the normally pigmented epidermis of patients with vitiligo. J Invest Dermatol 1982; 97:321-330
12. Le Poole I C, van den Wijngaard R M J G J, Westerhof W, Dutrieux R, Das P K. Presence or absence of melanocytes in vitiligo lesions: an immunohistochemical investigation. J Invest Dermatol 1993; 100:816-822
13. Le Poole I C, van den Wijngaard M J G J, Westerhof W, Das P K. Presence of T cells and macrophages in inflammatory vitiligo skin parallels melanocyte disappearance. Am J Pathol 1996; 148:1219-1228
14. Van den Wijngaard R, Wankowicz-Kalinska A, Le Poole C, Tigges B, Westerhof W, Das P. Local immune response in skin of generalized vitiligo patients. Destruction of melanocytes is associated with the prominent presence of CLA+ T cells at the perilesional site. Lab Invest 2000; 80:1299-1309
15. Van den Wijngaard R, Wankowicz-Kalinska A, Pals S, Weening J, Das P. Autoimmune melanocyte destruction in vitiligo. Lab Invest 2001; 81:1061-1067
16. Wankowicz-Kalinska A, van den Wijngaard R M, Tigges B J, Westerhof W, Ogg G S, Cerundolo V, Storkus W J, Das P K. Immunopolarization of CD4+ and CD8+ T cells to Type-1-like is associated with melanocyte lossinhumanvitiligo. Lab Invest. 2003; 83:683-95.
17. Boissy R E, Manga P. On the Etiology of Contact/Occupational Vitiligo. Pigment Cell Res. 17: 208-214, 2004
18. Cummings M P, Nordlund J J. Chemical leukoderma: fact or fancy. Am J Contact Dermatitis 1995; 6:122-127
19. Ortonne J-P, Bose S K. Vitiligo: where do we stand? Pigment Cell Res 1993; 6:61-72
20. Bleehen S S, Pathak M A, Hori Y, Fitzpatrick T B. Depigmentation of skin with 4-isopropylcatechol, mercaptoamines and other compounds. J Invest Dermatol 1968; 50:103-117
21. Gellin G A, Maibach H I, Misiaszek M H. Detection of environmental depigmenting substances. Contact Dermatitis 1979; 5:201-213
22. Miyamoto L, Taylor J S, Chemical leukoderma. In: Hann S-K, Nordlund J J, eds. Vitilogo: A Comprehensive Monograph on Basic and Clinical Science. Oxford: Blackwell Science Ltd; 2000. pp. 269-280
23. Riley P A. Melanogensis: a realistic target for antimelanoma therapy? Eur J Cancer 1991; 27:1172-1177
24. Riley P A. Melanogenesis and melanoma. Pigment Cell Res. 2003; 16:548-552
25. Yang F, Sarangarajan R, Le Poole I C, Medrano E E, Boissy R E. The cytotoxicity and apoptosis induced by 4-tertiary butylphenol in human melanocytes are independent of tyrosinase activity. J Invest Dermatol. 2000; 114 (1):157-64.
26. Riley P A. Mechanisms of inhibition of melanin pigmentation. In: Nordlund J J, Boissy R E, Hearing V J, King R A, Ortonne J-P, eds. The Pigmentary System. Physiology and Pathophysiology. New York: Oxford University Press; 1998. pp. 401-421
27. McGuire J, Hinders J. Biochemical basis for depigmentation of skin by phenol germicides. J Invest Dermatol 1971; 57:256-261
28. Jimbow K, Obata H, Pathak M A, Fitzpatrick T B. Mechanism of depigmentation by hydroquinone. J InvestDermatol 1974; 62:436-449
29. Thorneby-Andersson K, Sterner O, Hansson C. Tyrosinase-mediated formation of a reactive quinone from the depigmenting agents, 4-tert-butylphenol and 4-tert-butylcatechol. Pigment Cell Res. 2000; 13(1):33-8.
30. Lerner A. B., T. B. Fitzpatrick, E. Calkins, and W H. Summerson (1949) Mammalian tvrosinase: preparation and properties. J. Biol. Chem. 178:185-195.
31. Lerch K. (1981) Copper monooxygenases: Tyrosinase and dopamine hydroxylase. In: Metal lons in Biological Systems. H. Sigel, ed. New York. Marcel Dekker, Vol. 13, pp. 143-186.
32. Solomon, E I. and M. D. Lowery (1993) Ejectronic structure contributions to function in bioorganic chemistry. Science, 259:1575-1580.

33. Pomerantz, S. M. (1966) The tyrosine hydroxyiase activity of mammaljan tvrosinase. J. Bioi. Chem., 241:161-168.
34. Palumbo, A., M. d'Ischia, G. Misuraca, and G. Prota (1990) Activation of mammalian tyrosinase by ferrous ions. Biophys. Biochim. Acta, 1033:256-260.
35. Menter J. M., M. E. Townsel, C. L. Moore, G. D. Williamson, B. J. Soteres M. S. Fisher, and I. Willis (1990) Melanin accelerates the tyrosinase-cataiysed oxygenation of p-hydroxyanisole (MMEM). Pigment Cell Res., 3:90-97.
36. Osaki, S. (1963) The mechanism of tyrosine oxidation by mushroom tyrosinase. Arch. Biochim. Biophys., 100:378-384.
37. Kemp E H, Gawkrodger D J, MacNeil S, Watson P F, Weetman A P. Detection of tyrosinase autoantibodies in patients with vitiligo using 35S-labeled recombinant human tyrosinase in a radioimmunoassay. J Invest Dermatol 1997; 109: 69-73
38. Kemp E H, Waterman E A, Gawkrodger D J, Watson P F, Weetman A P. Autoantibodies to tyrosinase-related protein-1 detected in the sera of vitiligo patients using a quantitative radiobinding assay. Br J Dermatol 1998; 139:798-805
39. Kemp E H, Gawkrodger D J, Watson P F, Weetman A P. Immunoprecipitation of melanogenic enzyme autoantigens with vitiligo sera: evidence for cross-reactive autoantibodies to tyrosinase and tyrosinase-related protein-2 (TRP-2). Clin Exp Immunol 1997; 109:495-500
40. Kemp E H, Gawkrodger D J, Watson P F, Weetman A P. Autoantibodies to human melanocyte-specific protein pmel17 in the sera of vitiligo patients: a sensitive and quantitative radioimmunoassay (RIA). Clin Exp Immunol 1998; 114:333-338
41. Xie Z, Chen D. Jiao D, Bystryn J-C. Vitiligo antibodies are not directed to tyrosinase. Arch Dermatol 1999; 135: 417-422
42. Olivares C, Garcìa-Borron J C, Solano F. Identification of active site residues involved in metal cofactor binding and stereospecific substrate recognition in Mammalian tyrosinase, Implications to the catalytic cycle. Biochemistry 2002, 41, 679-686.

The invention claimed is:

1. A method of treating melanoma in a subject in need thereof, comprising:
   topically administering to said subject an effective amount of monobenzyl ether of hydroquinone; and
   administering to said subject an effective amount of imiquimod, said imiquimod being administered prior to, simultaneously with, or subsequent to the monobenzyl ether of hydroquinone.

2. The method according to claim 1, wherein the monobenzyl ether of hydroquinone is administered by topical administration of a composition that is suitable for transdermal delivery which composition comprises the monobenzyl ether of hydroquinone and wherein further excipients comprise at least a skin permeation enhancer or a release controlling polymer, matrix, coating or membrane.

3. The method according to claim 1, wherein the topical administration is by injection directly into a lesion.

4. The method according to claim 1, wherein the topical administration is around a lesion.

* * * * *